United States Patent [19]

Lee

[11] Patent Number: 5,613,502
[45] Date of Patent: Mar. 25, 1997

[54] PHOTO THERAPY EYE MASK

[76] Inventor: Mary S. Lee, 13040 Kiowa Rd., Apple Valley, Calif. 92308

[21] Appl. No.: 826,096

[22] Filed: Jul. 23, 1992

[51] Int. Cl.$^6$ .................................................. A61F 11/00
[52] U.S. Cl. .............................. 128/857; 128/858; 2/15
[58] Field of Search .......................... 128/858, 857, 128/846; 2/15, 10; 602/17

[56] References Cited

U.S. PATENT DOCUMENTS

| | | | |
|---|---|---|---|
| 945,839 | 1/1910 | Brisbane | 2/15 |
| 1,553,010 | 9/1925 | Terry | 2/15 |
| 2,874,385 | 2/1959 | Wade | 2/15 |
| 3,541,608 | 11/1970 | Otwell | 2/15 |
| 3,780,379 | 12/1973 | Kampman | 2/15 |
| 4,411,263 | 10/1983 | Cook | 2/15 |
| 4,502,476 | 3/1985 | Welt | 128/858 |
| 4,644,588 | 2/1987 | Zawacki | 2/15 |
| 4,790,031 | 12/1988 | Duerer | 128/858 |

*Primary Examiner*—Michael A. Brown
*Attorney, Agent, or Firm*—Christie, Parker & Hale, LLP

[57] ABSTRACT

This is an eye shield for babies undergoing phototherapy for hyperbilirubinemia. The part covering the eyes is a one piece protective mask in the shape shown. It is made from a three layered soft brushed nylon fabric. The attachment device is made from stretch gauze or knit material, gathered at the ends and attached to small Velcro tabs which in turn stick to the mask securing the gauze or knit material around the back of the head and the mask across the eyes as shown.

7 Claims, 1 Drawing Sheet

PHOTO THERAPY EYE MASK

BACKGROUND OF THE INVENTION

1. Field of the Invention

The invention relates to the field of eye shields, masks, protectors, specifically used to cover and protect the eyes of infants undergoing Photo Therapy treatment for hyperbilirubinemia.

The treatment consists of maximum skin exposure to bright blue fluorescent light rays for several days, until the blood bilirubin level declines. While the treatment is in progress the infant's eyes need to be covered and protected.

2. Description of the Prior Art

Prior methods used to protect the infant's eyes are less than satisfactory. Some methods are cumbersome and awkward requiring skill and patience to put on correctly and constant vigilance to make sure the eye protector stays in place, all very time consuming, some use adhesive means which stick to the infant's skin causing irritations, abrasions, and skin break down when removed, some require a very snug fit to keep the mask secure and in place possibly obscuring the infant's nares (due to the soft cartilage in an infant's nose) leading to apnea and even more severe consequences and some have no way to adjust to the size and shape of different infant's heads, most allow for unnecessary eye exposure.

SUMMARY OF THE INVENTION

This invention intends to prove maximum eye protection, with minimum skin coverage and minimum danger to the infant. The eye covering is in the generalized shape of typical eye covering, it has a soft nappy surface on both sides making it reversible and the inner layer is black flexible material providing maximum light blockage. The attachment system is unique and eliminates the disadvantages of the prior methods. The mesh gauze is a single layer of open weave stretch netting, gathered at each end with a small piece of Velcro attached at the gathered ends. The eye covering goes over the infant's eyes, the netting is opened up over the back of the infant's heads, like a baby bonnet, and the Velcro at each end is stuck to the eye covering holding it in place. The process is very quick and easy to accomplish, there is nothing that sticks to the infant's skin, and there is no need to pull the device tight to keep it in place. The open weave of the stretch gauze allows even the skin of the scalp exposure to the light but keeps the eyes covered with maximum protection and minimal danger.

DESCRIPTION OF THE PREFERRED EMBODIMENT

The preferred embodiment is illustrated and described in the application contained herein, let it be understood that variations will be apparent to those skilled in the art without departing from the principles of the invention. Therefore, the invention shall not be limited to the specific form as described and illustrated but rather limited only by the literal interpretation of the claims herein.

Figure 1:
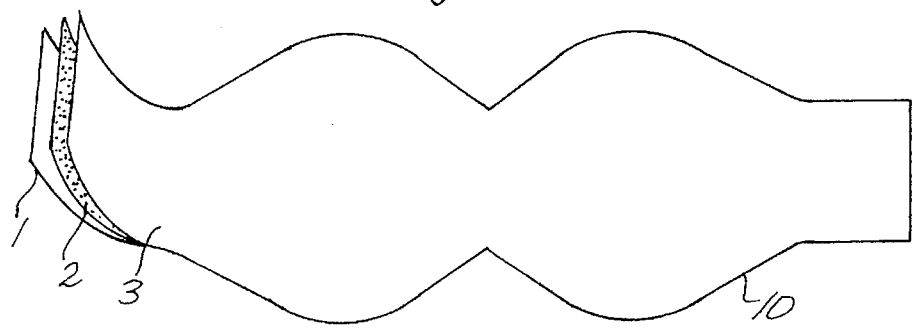
FIG. 1 illustrates eye covering (mask) with 3 layers.

FIG. 1 illustrates the one piece eye covering or mask 10, in a plain view, demonstrating the fact that it is comprised of three layers, ( 1&3 ) two soft napped outer layers 1, 3 and one black flexible inner layer 2. The approximate size of the mask is 16 cm. in length, varying to accommodate two sizes.

Figure 2:
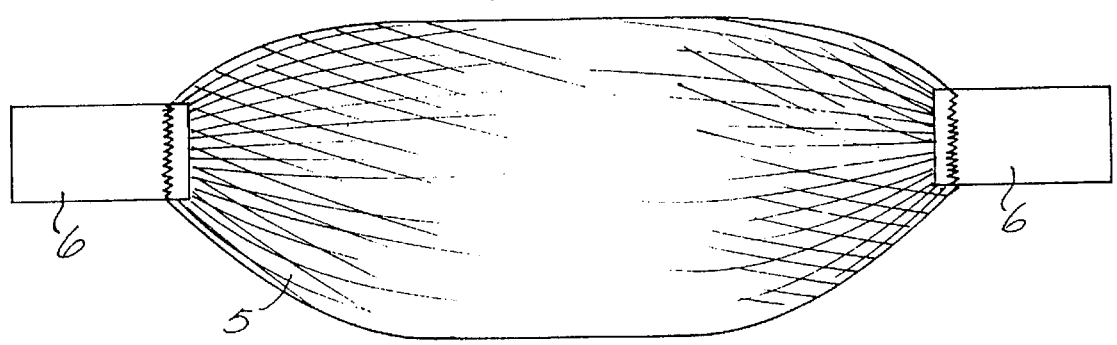
FIG. 2 illustrates the attachment device inclusive of the gathered stretch netting with the Velcro tabs at each end.

FIG. 2 illustrates the one piece attachment device 4 with the stretch netting 5 gathered at both ends and the Velcro tabs 6 in place. The approximate size of the Velcro tabs is 1½ cm.×4 cm., and the approximate size of the stretch netting is 11 cm.×16 cm., varying with to accommodate two sizes and differences in give and stretch of materials available.

Figure 3:
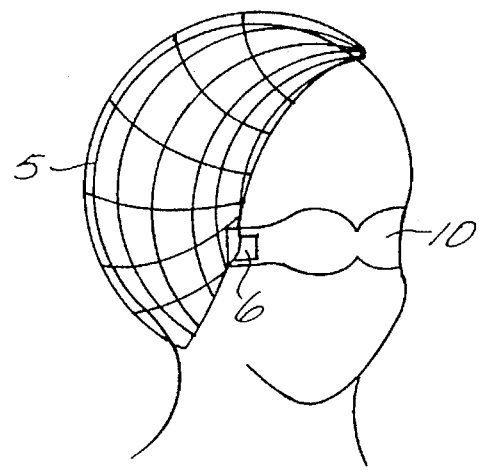
FIG. 3 illustrates the eye shield as worn by an infant.

FIG. 3 illustrates the two piece Photo Therapy Eye Mask (Bili Bonnet) as seen on the infant, eye covering (mask) in place, with Velcro tabs 6 stuck to the mask 10 and stretch netting 5 surrounding the back of the infant's head and holding mask in place.

I claim:

1. An infant eye shield for protecting an infant's eyes from phototherapy treatment light comprising:

an eye piece having two interconnected oval shape areas for completely covering an infant's eyes, the eye piece being made of a material having one member of a hook and loop fastener and including an opaque layer; and an attachment means comprising a strip of stretchable open work fabric gathered at its ends, forming a hammock shaped support for contact with only a portion of the back of the infant's head, and the other member of a hook and loop fastener attached to each end of the fabric for attachment to the hook and loop fastener on the eyepiece.

2. The infant eye shield of claim 1 wherein the eyepiece comprises an opaque layer sandwiched between two soft, flexible fabric layers.

3. The eye shield of claim 2 wherein the eyepiece is reversible.

4. The eye shield of claim 1 wherein a pad with the hook member of a hook and loop fastener is attached to each end of the strip of stretchable open work fabric.

5. An infant eye shield for protecting an infant's eyes from phototherapy treatment light comprising:

an eye piece having two interconnected oval shaped areas for completely covering the infant's eyes, and a flap extending from each side of the eyepiece for accommodating different positions of an attachment means, the eye piece being made of a material including the loop member of a hook and loop fastener, and including an opaque layer;

a strip of stretchable open work fabric, forming a hammock shaped support for contact with a portion of the back of the infant's head, a pad with the hook member of a hook and loop fastener attached to each end of the strip of fabric for attachment to the loop member of the eyepiece; and stitching between each pad and the adjacent end of the strip engaging a gathered end of the strip, thereby preventing stretching of the end of the strip, whereby a center portion of the strip is stretchable for forming a hammock shaped net behind the head of an infant wearing the eye piece over its eyes.

6. The infant eye shield of claim 5 wherein the eyepiece comprises an opaque layer sandwiched between two soft, flexible fabric layers.

7. The eye shield of claim 6 wherein the eyepiece is reversible.

* * * * *